United States Patent [19]
Findeisen et al.

[11] Patent Number: 4,570,009
[45] Date of Patent: Feb. 11, 1986

[54] PROCESS FOR PREPARING DIMETHYLSILYL DICYANIDE

[75] Inventors: Kurt Findeisen, Odenthal; Rudolf Fauss, Cologne, both of Fed. Rep. of Germany

[73] Assignee: Bayer Aktiengesellschaft, Leverkusen, Fed. Rep. of Germany

[21] Appl. No.: 669,192

[22] Filed: Nov. 7, 1984

[30] Foreign Application Priority Data

Nov. 25, 1983 [DE] Fed. Rep. of Germany ....... 3342690

[51] Int. Cl.$^4$ .............................................. C07F 7/10
[52] U.S. Cl. .................................................. 556/415
[58] Field of Search ....................................... 556/415

[56] References Cited

U.S. PATENT DOCUMENTS 4,328,351 5/1982 Findeisen et al. .................. 556/415
4,429,145 1/1984 Reetz et al. ........................ 556/415

OTHER PUBLICATIONS

J. Hundeck, "Zur Darstellung von Methyl- und Methyl-dialkylamino-cyanosilanen", Zeitschrift für Anorganische und Allgemeine Chemie, vol. 345, (1966), pp. 23-28.

Primary Examiner—Paul F. Shaver
Attorney, Agent, or Firm—Sprung, Horn, Kramer & Woods

[57] ABSTRACT

A process for preparing dimethylsilyl dicyanide comprising reacting trimethylsilyl cyanide with dimethylsilyl dichloride. Advantageously the trimethylsilyl chloride formed as a by-product in the course of the reaction is continuously removed from the reaction, the trimethylsilyl cyanide starting material is produced by reacting trimethylsilyl chloride with an alkali metal cyanide, and the by-product trimethylsilyl chloride of the principal reaction is recycled to the preparation of trimethylsilyl cyanide.

6 Claims, No Drawings

PROCESS FOR PREPARING DIMETHYLSILYL DICYANIDE

The present invention relates to a new process for preparing dimethylsilyl dicyanide.

It is known to prepare dialkylsilyl dicyanides by reacting dialkylsilyl dichlorides with silver cyanide. The starting materials used in this process are costly. The process produces high yields only if the reactions are carried out for a long time (Synthesis 1978, page 154).

It has now been found that dimethylsilyl dicyanide is obtained when dimethylsilyl dichloride is reacted with trimethylsilyl cyanide.

This reaction was surprising, since, although trimethylsilyl chloride can be reacted at between 130° and 250° C. in aprotic solvents with alkali metal cyanide in the presence of heavy metal cyanides as the catalysts, dimethylsilyl dichloride does not react under the same conditions to produce the desired dimethylsilyl dicyanide.

It was therefore astonishing that the reaction of dimethylsilyl dichloride with trimethylsilyl cyanide proceeds without difficulties and in high yields.

Using the process according to the invention it is thus possible to obtain dimethylsilyl dicyanide in a faster and less costly manner than using the existing processes.

The course of the reaction of the process according to the invention can be represented by the following reaction equation:

$$(CH_3)_2SiCl_2 + 2(CH_3)_3SiCN \rightarrow (CH_3)_2Si(CN)_2 + 2(CH_3)_3SiCl$$

To carry out the reaction the starting materials are brought together and heated. However, it is also possible to introduce either of the two starting materials first and to meter in the other component at the desired reaction temperature.

Preferably, trimethylsilyl cyanide is introduced first, and is heated to reaction temperature, and dimethylsilyl dichloride is then added.

At least 2 moles of trimethylsilyl cyanide, preferably 2.2–6 moles of trimethylsilyl cyanide, are used per mole of dimethylsilyl dichloride.

The reaction is carried out at between 50° and 250° C., preferably at between 80° and 180° C. It is particularly preferable to carry out the reaction at the boiling point of the reaction mixture.

The reaction proceeds satisfactorily even in the absence of catalysts and auxiliaries. However, it is preferable to use catalysts of the Lewis acid type, such as, for example, aluminum chloride, iron(III) chloride, antimony(V) chloride, boron trifluoride, titanium(IV) chloride, zinc chloride, tin(IV) chloride, copper(I) chloride, copper(I) cyanide, zinc iodide and mixtures of these compounds. Particularly preferred catalysts are aluminum chloride, iron(III) chloride, zinc chloride and their mixtures.

Normally, the reaction is carried out in the absence of solvents. In certain cases it can be advisable to use solvents which are inert to products and educts.

Specific examples of solvents are toluene, chlorobenzene, dichlorobenzene, trichlorobenzene, nitrobenzene, tetramethylene sulphone, tetramethylurea and N-methylpyrolidone.

The reaction is carried out under atmospheric pressure, but in certain cases it can also take place under reduced or superatmospheric pressure.

The trimethylsilyl chloride formed in the course of the reaction is preferably continuously distilled off during the reaction. The reaction can be carried out not only continuously but also discontinuously. The preparation of dimethylsilyl dicyanide can be coupled directly to the synthesis of trimethylsilyl cyanide, In this case the reaction equations can take the following form:

$$2(CH_3)_3SiCl + 2NaCN \rightarrow 2(CH_3)_3SiCN + 2NaCl \quad \text{(Eq. 1)}$$

$$2(CH_3)_3SiCN + (CH_3)_2SiCl_2 \rightarrow 2(CH_3)_3SiCl + (CH_3)_2Si(CN)_2 \quad \text{(Eq. 2)}$$

$$(CH_3)_2SiCl_2 + 2NaCN \rightarrow (CH_3)_2Si(CN)_2 + 2NaCl \quad \text{(Eq. 3)}$$

Taking equation 1 and equation 2 together produces equation 3.

There now follows a description of how the process according to the invention is carried out when coupled to the preparation of trimethylsilyl cyanide. Trimethylsilyl cyanide is obtained in high yield by reacting trimethylsilyl chloride at temperatures between 130° and 250° C. with an approximately equimolar amount of an alkali metal cyanide in the presence of a catalytic amount of a heavy metal cyanide and in the presence of an aprotic solvent which boils at above 150° C., and removing trimethylsilyl cyanide from the reaction mixture by distillation at the same rate at which it is being formed, separating, by evaporation, from the trimethylsilyl cyanide any unreacted trimethylsilyl chloride which is distilled over at the same time, and recycling it into the reaction vessel until all of it has reacted (compare German Offenlegungsschrift 3,018,821).

If dimethylsilyl dichloride is then introduced into the trimethylsilyl cyanide distilled out of the reaction, the trimethylsilyl cyanide immediately reacts further to trimethylsilyl chloride, and dimethylsilyl dicyanide is formed. The trimethylsilyl chloride which is formed in the course of this step is separated off by distillation together with the unreacted portion from the synthesis of the trimethylsilyl cyanide and is recycled.

The trimethylsilyl chloride is thus recycled. The ease with which trimethylsilyl chloride is separated off can be assessed by using an appropriate apparatus, for example an efficient column.

The crude product obtained is worked up by distillation, which—to avoid bottom temperatures over 200° C.—advisably takes the form of distilling over the almost pure dimethylsilyl dicyanide, left behind once the fore-runnings have been removed, at some speed, if necessary under reduced pressure.

The reaction is ideally carried out in such a way that all of the dimethyldichlorosilane is reacted. This is achieved, for example, by introducing dimethylsilyldichlorosilane into a reaction solution which is being thoroughly stirred.

However, it is also possible to separate off, using an efficient column, any unreacted dimethyldichlorosilane entrained with the trimethylsilyl chloride, and to recycle it.

EXAMPLE 1

2,000 g (20 moles) of trimethylsilyl cyanide and 5 g of $ZnCl_2$ were heated to the reflux temperature, and 1,032 g (8 moles) of dimethylsilyl dichloride were gradually added dropwise. The resulting trimethylsilyl chloride was continuously distilled off over a 30 cm packed column. The bottom product was then worked up by distillation. The fore-runnings were first trimethylsilyl chloride and then excess trimethylsilyl cyanide. The bottom product was then worked up by distillation without a packed column. 730 g of dimethylsilyl dicyanide were speedily distilled over at a boiling point of 165°–175° C.

EXAMPLE 2

200 g (4 moles) of 98% strength sodium cyanide and 20 g (0.22 mole) of copper(I) cyanide were introduced into 1,000 ml of dry tetramethylene sulphone in a 4-liter four-necked flask equipped with a stirrer, a thermometer, an inlet tube connected to a stock reservoir vessel for $(CH_3)_3SiCl$, and a short column placed on top, and the mixture was heated to 180° to 190° C. 488 g (4.5 moles) of trimethylsilyl chloride (purity as determined by gas chromatography: 98.6%) was obtained at said temperature. The trimethylsilyl cyanide formed in the course of the reaction was continuously passed out of the reaction mixture by way of the attached short column and a subsequent distillation bridge and introduced into a 2-liter four-necked flask equipped with a stirrer, a thermometer, a connection tube to the abovementioned distillation bridge, and an attached 60 cm packed column, and a bottom discharge valve, and held at 90° C.

During the reaction a total of 1,000 g (20 moles) of sodium cyanide were added in 3 portions to the sulpholane bottom in line with the consumption.

3 g of $ZnCl_2$ were placed beforehand in the receiving flask (2-liter four-necked flask).

When almost the entire trimethylsilyl chloride had been reacted, the contents of the receiving flask were heated to the reflux temperature. 1,300 g (10 moles) of dimethylsilyl dichloride were then pumped with vigorous stirring to underneath the surface of the liquid in the course of 10 hours.

The trimethylsilyl chloride formed in the course of the reaction of dimethylsilyl dichloride in the receiving flask and that carried over in trimethylsilyl cyanide distilled off was separated off by distillation over the packed column and was returned into the stock reservoir vessel and was hence recycled into the reaction vessel for reaction with the sodium cyanide. During the reaction the bottom temperature in the receiving flask under reflux conditions rose from 110° to about 130° C.

When all the sodium cyanide had reacted, a forerunning was taken out of the receiving flask by way of the column (boiling point 62°–118° C.; 220 g; 90% trimethylsilyl cyanide, and 10% trimethylsilyl chloride, according to GC).

The bottom product, which was still warm, was then transferred by way of the bottom discharge valve into a 2-liter flask (10 cm Vigrieux column, and distillation bridge) and was worked up by distillation:

| Fraction | Pressure (mm Hg) | Temperature | Amount |
|---|---|---|---|
| 1 | 760 | 120–142 | 120 g |
| 2 | 760 | –160 | 70 g |
| 3 | 14 | 60–70 | 935 g |

Fraction 1 was analyzed by gas chromatography (trimethylsilyl cyanide), and fractions 2 and 3 were analyzed by nuclear magnetic resonance spectroscopy. Fraction 2 consisted of trimethylsilyl cyanide and dimethylsilyl dicyanide in a molar ratio of 30:70. Fraction 3 only consisted of dimethylsilyl dicyanide.

The yield of dimethylsilyl dicyanide, relative to starting dimethylsilyl dichloride, was 85% of theory.

EXAMPLE 3

1,000 g (10 moles) of trimethylsilyl cyanide were refluxed, and 516 g (4 moles) of dimethylsilyl dichloride were gradually added dropwise. The mixture was refluxed for 6 hours. Thereafter, first trimethylsilyl chloride and then excess trimethylsilyl cyanide were distilled off over a 30 cm packed column. 360 g of dimethylsilyl dicyanide were then speedily distilled over via a bridge at a boiling point of 165°–175° C.

It will be understood that the specification and examples are illustrative but not limitative of the present invention and that other embodiments within the spirit and scope of the invention will suggest themselves to those skilled in the art.

What is claimed:

1. A process for preparing dimethylsilyl dicyanide comprising reacting trimethylsilyl cyanide with dimethylsilyl dichloride.

2. A process according to claim 1, wherein the trimethylsilyl chloride formed as a by-product in the course of the reaction is continously removed from the reaction.

3. A process according to claim 1, wherein the reaction is effected in the presence of a Lewis acid as catalyst.

4. A process according to claim 1, wherein the reaction is carried out between about 50° and 250° C.

5. A process according to claim 2, wherein the trimethylsilyl cyanide starting material is produced by reacting trimethylsilyl chloride with an alkali metal cyanide, and the by-product trimethylsilyl chloride of the principal reaction is recycled to the preparation of trimethylsilyl cyanide.

6. A process according to claim 5, wherein the reaction is effected in the presence of a Lewis acid as catalyst and the reaction is carried out between about 50° and 250° C.

* * * * *